United States Patent [19]
Horwitz et al.

[11] Patent Number: 5,332,531
[45] Date of Patent: Jul. 26, 1994

[54] EXTRACTING METAL IONS WITH DIPHOSPHONIC ACID, OR DERIVATIVE THEREOF

[75] Inventors: Earl P. Horwitz; Ralph C. Gatrone; Kenneth L. Nash, all of Argonne, Ill.

[73] Assignee: Arch Development Corporation, Chicago, Ill.

[21] Appl. No.: 898,386

[22] Filed: Jun. 10, 1992

Related U.S. Application Data

[60] Division of Ser. No. 351,402, May 12, 1989, abandoned, which is a continuation-in-part of Ser. No. 265,608, Nov. 1, 1988, abandoned.

[51] Int. Cl.$^5$ .................. C01G 56/00; C01G 1/00
[52] U.S. Cl. .................. 588/20; 423/9; 423/10; 423/11; 423/21.5; 423/24; 423/42; 423/112; 423/139; 423/140; 423/122; 423/157; 423/158; 423/181; 423/184; 423/658.5
[58] Field of Search .................. 252/631; 423/9, 10, 423/11, 21.5, 24, 42, 112, 139, 140, 122, 157, 158, 181, 184, 658.5

[56] References Cited

U.S. PATENT DOCUMENTS

| | | | |
|---|---|---|---|
| 2,686,803 | 8/1954 | Stayner | 260/461 |
| 3,520,808 | 7/1970 | Light | 252/46.6 |
| 3,617,576 | 11/1971 | Kerst | 210/58 |
| 3,625,982 | 12/1971 | Christensen | 260/348 P |
| 3,641,126 | 2/1972 | Prentice | 260/502.4 A |
| 3,808,237 | 4/1974 | Littleton | 260/348 R |
| 3,940,436 | 2/1976 | Kerst | 260/502.5 |
| 3,993,728 | 11/1976 | Schulz | 423/9 |
| 4,075,291 | 2/1978 | Redmore et al. | 260/933 |
| 4,254,063 | 3/1981 | Becker | 260/931 |
| 4,293,529 | 10/1981 | Reese et al. | 423/10 |
| 4,302,429 | 11/1981 | Lawes et al. | 423/17 |
| 4,316,877 | 2/1982 | Tunick et al. | 423/10 |
| 4,460,548 | 7/1984 | Sturtz | 423/10 |
| 4,464,346 | 8/1984 | Sturtz et al. | 423/10 |
| 4,499,833 | 2/1985 | Grantham | 252/631 |
| 4,579,720 | 4/1986 | Budnick | 423/10 |
| 4,645,762 | 2/1987 | Biere et al. | 514/108 |
| 4,656,012 | 4/1987 | Jdid et al. | 423/10 |
| 4,733,005 | 3/1988 | Schmidt et al. | 560/222 |
| 4,762,649 | 8/1988 | Coleman | 260/545 P |
| 4,828,766 | 5/1989 | Kleeman et al. | 260/502.4 P |
| 4,876,248 | 10/1989 | Breliere et al. | 514/108 |
| 4,908,138 | 3/1990 | Blum et al. | 210/700 |
| 4,927,814 | 5/1990 | Goll et al. | 514/108 |

FOREIGN PATENT DOCUMENTS

| | | |
|---|---|---|
| 301351 | 2/1989 | European Pat. Off. . |
| 790698 | 12/1981 | U.S.S.R. . |
| 1204967 | 9/1970 | United Kingdom . |
| 1345518 | 1/1974 | United Kingdom .................. 562/21 |

Primary Examiner—Edward A. Miller
Attorney, Agent, or Firm—Frishauf, Holtz, Goodman & Woodward

[57] ABSTRACT

Thermodynamically-unstable complexing agents which are diphosphonic acids and diphosphonic acid derivatives (or sulphur containing analogs), like carboxyhydroxymethanediphosphonic acid and vinylidene-1,1-diphosphonic acid, are capable of complexing with metal ions, and especially metal ions in the II, III, IV, V and VI oxidation states, to form stable, water-soluble metal ion complexes in moderately alkaline to highly-acidic media. However, the complexing agents can be decomposed, under mild conditions, into non-organic compounds which, for many purposes are environmentally-nondamaging compounds thereby degrading the complex and releasing the metal ion for disposal or recovery. Uses for such complexing agents as well as methods for their manufacture are also described.

34 Claims, 1 Drawing Sheet

EXTRACTING METAL IONS WITH DIPHOSPHONIC ACID, OR DERIVATIVE THEREOF

The U.S. Government has rights in this invention pursuant to Contract No. W-31-109-ENG-38 between the U.S. Department of Energy and University of Chicago as operator of Argonne National Laboratory.

This application is a Division of application Ser. No. 07/351,402, filed May 12, 1989 (abandoned), which is a continuation-in-part application of U.S. application Ser. No. 265,608 filed Nov. 1, 1988 (now abandoned).

The present invention relates to thermodynamically-unstable complexing agents and methods of manufacture and use.

More particularly, the present invention relates to diphosphonic acid, or derivative thereof (or sulphur containing analogs), complexing agents for metal ions having an oxidation state of II, III, IV, V, or VI, in a moderately alkaline to highly-acidic medium to form water-soluble complexes. Metals for which complexes can be formed include uranium, iron, aluminum, vanadium, chromium and rare earths.

The thermodynamically-unstable complexing agents of the present invention can be decomposed into non-organic compounds, such as water, carbon dioxide, phosphoric acid and sulfuric acid using relative mild conditions. Mild conditions include mild oxidizing conditions with oxidizing agents, such as hydrogen peroxide or nitric acid, heating to moderately elevated temperatures, such as from about 50° C. to the boiling point of the aqueous medium in which they are used, for a short period of time, or even autodecomposition at ambient temperature for a day or two.

The complexing agents of the present invention can be used as aqueous extraction agents or hold-back agents. They are particularly useful in liquid-liquid solvent extraction processes where they can be used as hold-back agents for improving the selectivity of an organic extraction solvent in removing one or more particular metal ion or other organic extractable component from an aqueous solution that includes a variety of metal ions or a mixture of metal ions and other organic extractable components. The complexed metal can then be released by decomposition of the complex. The compounds formed by decomposition of the complexing agent are non-organic easily handled or disposed of compounds. The released metal ions can be easily extracted for concentration or, depending on concentration and conditions, can be removed as a phosphate salt precipitate. These properties are particularly useful for concentration and disposal of radioactive metals.

BACKGROUND OF THE INVENTION AND PRIOR ART

Inorganic complexing agents and organic complexing agents are well-known and have been used extensively in numerous industrial applications. Generally, complexing agents are used either to help remove metal ions from solution or to help solubilize metal ions in solution. The variety of complexing agents that have been developed demonstrates that no one particular complexing agent or class of complexing agents has performed satisfactorily across all industries to remove and/or solubilize all metal ions in all applications. Therefore, specific complexing agents were developed to solve particular industrial application problems. However, these specific metal complexing agents, in general, have the disadvantage of small effective pH range, persisting in the environment and/or adversely affecting the environment. Most cannot be used in very acid media such as media in the pH range of 2 or less.

A known class of efficient chelating agents are the phosphonic acids and diphosphonic acids, generally characterized by the structural formulas, $RCH_2PO_3H_2$ and $RCH(PO_3H_2)_2$, wherein R is an alkyl, aryl, substituted alkyl, or substituted aryl group. The phosphonic acid and diphosphonic acid compounds, although effective as complexing agents, also possess disadvantages. One particular disadvantage is their excellent thermodynamic stability. Although thermodynamic stability normally is desirable in industrial compounds, such stability is a definite disadvantage after the complexing action is no longer desirable as when recovery of the complexed metal from solution is required.

Complexing agents are useful, for example, for clearing waste effluent streams from industrial processing and manufacturing. Another example is the case where one or more environmentally-damaging and/or toxic metal ions, such as radioactive metal ions or metal ions such as cadmium or zinc are intermixed with one or more non-damaging and/or non-toxic metal ions. Selective removal of the cadmium or zinc reduces disposal costs. A further example is the situation where a waste stream contains several different metal ion species wherein only one or two of the metal ions species are sufficiently valuable to justify separation of the metal ion from the waste stream for eventual isolation, regeneration and reuse. In each case, it is desirable to be able to remove selected metal ions and recover them or concentrate them for disposal.

Among the most objectionable byproducts is radioactive waste. The most toxic constituents in radioactive waste are the highly radioactive transuranic elements, i.e., the man-made elements heavier than uranium, that have extremely long half-lives and keep nuclear wastes toxic for millions of years. Currently, disposal of such highly toxic radioactive wastes requires converting the radioactive waste into a glass via vitrification, then burying the glass in deep geologic mines or repositories. Millions of gallons of waste that contain transuranic elements are currently awaiting such a disposal treatment.

DETAILED DESCRIPTION OF THE INVENTION

Figure 1:
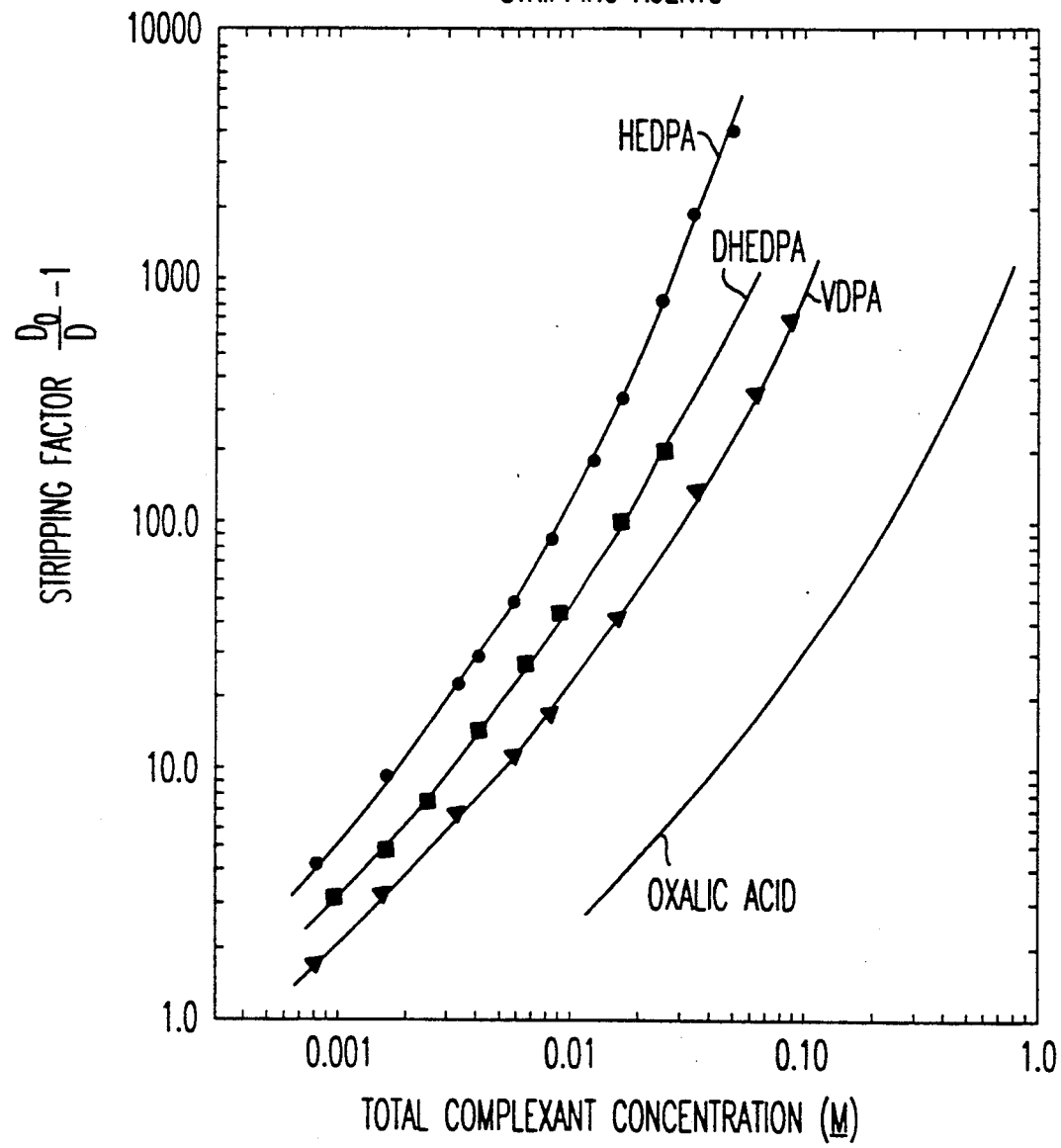
FIG. 1 is a graph of the stripping factor (DO/D-1) for the metal ion europium III (Eu(III)) vs. the total molar concentration of a complexing agents for the stripping of Eu(III) ions from aqueous solutions by various thermally-unstable complexing agents of the present invention and by oxalic acid.

The thermodynamically-unstable compound of the present invention is generally represented by one of the following structural formulas:

Metal complexes formed thereby can be represented as follows:

| M(II) | M(III) | M(IV) | M(V) | M(VI) |
|---|---|---|---|---|
| $M(H_3L)_2$ | $M(H_3L)_2{}^+$ | $M(H_3L)_2{}^{2+}$ | $MO_2(H_3L)_2{}^-$ | $MO_2(H_3L)_2$ |
| $M(H_3L)^+$ | $M(H_3L)^{2+}$ | $M(H_3L)^{3+}$ | $MO_2(H_3L)$ | $MO_2(H_3L)^+$ |
| $M(H_2L)_2{}^{2-}$ | $M(H_2L)_2{}^-$ | $M(H_2L)_2{}^+$ | $MO_2(H_2L)_2{}^{3-}$ | $MO_2(H_2L)_2{}^{2-}$ |
| $M(H_2L)$ | $M(H_2L)^+$ | $M(H_2L)^{2+}$ | $MO_2(H_2L)^-$ | $MO_2(H_2L)$ |
| | | $M(H_3L)_3{}^+$ | | |
| | | $M(H_2L)_3{}^{2-}$ | | |
| | | ML | | |
| | | $ML_2{}^{4-}$ | | | wherein $H_4L$ is one of the compounds represented above. Preferably, M is an actinide, a lanthanide, Sr, Mo, or Zr. However, other metal ions can also be complexed including, for example, Fe, as described below in the Examples.

In the field of liquid-liquid extractions, such as in treating radioactive liquid wastes, the efficient extraction of a particular metal ion species from a solution that includes a number of different metal ion species is a primary goal. Therefore, a need for a complexing agent that preferentially complexes with certain metal ion species of interest to form a stable, water-soluble metal complex that resists extraction, thereby allowing removal of the other interfering metal ion species in solution by standard liquid-liquid separation techniques. Conversely, the complexing agent can form a stable, water-soluble complex with a metal ion species not of interest, such that the particular ion of interest can be removed by standard liquid-liquid extraction techniques and thereby recovered, regenerated and recycled; or, in the case of a harmful, toxic and/or radioactive metal ion, for removal and subsequent proper disposal.

Therefore, in accordance with an important feature of the present invention, complexing agents are provided that, when introduced into a waste or feed stream that contains a variety of metal ions, overcome the disadvantages of the prior art complexing agents in regard to liquid-liquid metal ion extractions performed at pH values ranging from about ten to pH values demonstrated by 7M strong acids. This includes the pH range of 2 or less where there are few if any generally useful complexing agents. The complexing agents of the present invention unexpectedly possess the properties of being water soluble; forming highly stable complexes with metal ions, including metal ions in the II, III, IV, V and VI oxidation states in very acidic media, such as media that is 7M in strong acid, like 7M nitric acid; complexing with metal ions to form water-soluble metal complexes; and having the ability, either before or after complexing with the metal ion, to readily decompose to non-organic and essentially environmentally-nondamaging and non-noxious compounds under mild conditions.

The complexing agents of the present invention possess all of the above-listed properties. They form very stable complexes but are themselves thermodynamically unstable and degrade relatively rapidly to environmentally-nondamaging compounds. Thus the metal ion can be released from the stable complex by destroying the complexing agent. The term environmentally-nondamaging compound, as used here and hereinafter, refers to environmentally innocuous compounds, like water and carbon dioxide, and to compounds that are fully degraded, such as phosphoric acid or sulfuric acid, and therefore do not pose long term waste and disposal

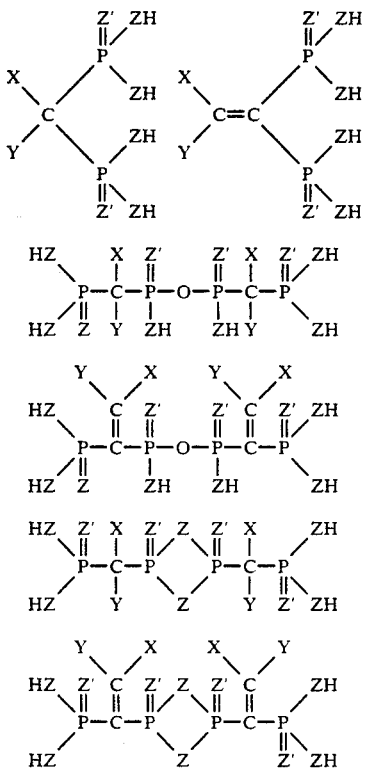

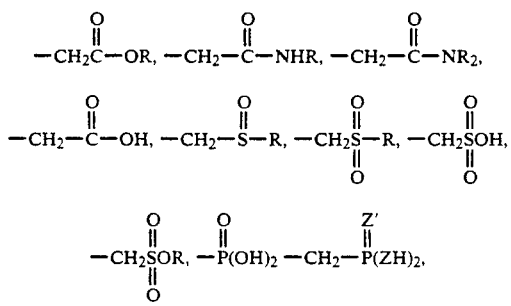

wherein the X and Y substituents are each selected from the group consisting of —H, halogen, —Z″H, —CO₂H, —CH₂Z″H, —CH₃, —CH₂CH₃, —CH₂NH₂, —CONH₂, —CH₂Cl, —CH₂Be, —CH₂F, —CH₂I, —CH₂NO₂, —CH₂CN, —CH₂OR, —CH₂SR, $$-CH_2\overset{O}{\overset{\|}{C}}-OR,\ -CH_2-\overset{O}{\overset{\|}{C}}-NHR,\ -CH_2-\overset{O}{\overset{\|}{C}}-NR_2,$$

$$-CH_2-\overset{O}{\overset{\|}{C}}-OH,\ -CH_2-\overset{O}{\overset{\|}{S}}-R,\ -CH_2-\overset{O}{\underset{\overset{\|}{O}}{\overset{\|}{S}}}-R,\ -CH_2\underset{\overset{\|}{O}}{\overset{\|}{S}}OH,$$

$$-CH_2\underset{\overset{\|}{O}}{\overset{\|}{S}}OR,\ -\overset{O}{\overset{\|}{P}}(OH)_2\ -CH_2-\overset{Z'}{\overset{\|}{P}}(ZH)_2,$$

and —CH(PO₃H₂)₂, wherein
R is an alkyl group with one to three carbon atoms;
Z is oxygen or sulphur;
Z′ is oxygen or sulphur; and
Z″ is oxygen or sulphur;
or a salt, ester or thioester thereof.

problems. Furthermore, these degradation products can be non-noxious for human consumption in small amounts thereby reducing problems in the use of the invention complexing agents in treating materials intended for human (or animal) consumption.

Complexing agents possessing all of these properties are new and unexpected in the art because normally, in highly acidic media, such as media corresponding to acid concentrations of pH 2 up to 7 molar in strong acid such as nitric acid, metal complexation is inefficient or impossible because most complexing agents are not capable of preferentially complexing with a metal ion as opposed to the hydrogen ions in solution. In effect, the overwhelming abundance of hydrogen ions in acidic media simply overcome the ability of the complexing agent to complex with the metal ions in solution.

Surprisingly, and as will be discussed more fully hereinafter, the thermally-unstable complexing agents of the present invention outperform most known complexing agents in highly acidic media, and are especially useful in media with a pH of 2 or less. Prior art complexing agents that can be made to form metal complexes at low pH values usually form water-insoluble metal complexes, therefore making the separation of the complexed metal ion from solution more difficult because liquid-solid separation techniques are required, as opposed to the more efficient and economical liquid-liquid extraction techniques. In addition, the thermodynamically-unstable complexing agents of the present invention have a degree of thermodynamic instability designed into the compound, such that either in its uncomplexed state or after complexing with a metal, the thermodynamically-unstable complexing agent is destroyed by autodecomposition or under mild thermal conditions both to destroy any excess complexing agent in the solution and to release the complexed metal ion back into the solution for easier and more efficient subsequent separation and disposal, or regeneration and recycle, of the metal ion. Furthermore, the thermodynamically-unstable complexing agents of the present invention degrade into inorganic and substantially environmentally-nondamaging compounds, therefore avoiding additional waste disposal problems.

A complexing agent having the above-described combination of properties can be used in liquid-liquid extractions or in supported liquid membrane processes to separate metal ion species in solution. For example, the thermodynamically-unstable complexing agents of the present invention can be used as holdback reagents. Holdback reagents are used to improve the selectivity of extraction solvents by strongly complexing with particular polyvalent metal ions, thereby permitting the more selective extraction of other metal ion species (that form less stable complexes with the holdback reagent) from the solution. One example of using complexing agents as hold back reagents is the previously described method of treating a high-level nuclear waste stream including americium, curium, plutonium and neptunium ions. In a similar application, oxalic acid is used to preferentially complex the fission products zirconium and molybdenum, thereby increasing extraction solvent selectivity for the americium ion that forms a much less stable oxalato complex than zirconium and molybdenum ions. However, oxalic acid is not a sufficiently strong acid to effectively complex zirconium and molybdenum ions in solutions having an acidity greater than 2 molar $HNO_3$. Therefore, the application of oxalic acid as a complexing agent is limited. However, the thermodynamically-unstable complexing agents of the present invention have lower acid dissociation constants ($pK_a$ values), and therefore are stronger acids, than oxalic acid and are not limited like oxalic acid. In addition, the thermodynamic instability of the thermodynamically-unstable complexing agents avoids the subsequent disposal and environmental problems that the more stable complexing agents, e.g., oxalic acid and the aminopolycarboxylic acids, create.

In general, the aqueous immiscible extraction solvents used herein are well-known organic soluble agents commonly used in the type of liquid-liquid extractions as required here. These are different than the aqueous soluble complexing agents of the invention and are organic compounds such as neutral and acidic organophosphorus compounds, alkyl amines, and quaternary ammonium chlorides. Examples of such extraction solvents are mono(2-ethylhexyl) 2-ethylhexylphosphonic acid, bis(2,5,5-trimethylpentyl)phosphinic acid, tributyl phosphate, trioctyl amine, bis(2-ethylhexyl) phosphoric acid, and octyl(phenyl)-N,N-diisobutylcarbamoylmethylphosphine oxide. Other alkyl amines, oxide. Other alkyl amines, dialkyl amines, trialkyl amines and organophosphorus acid compounds also are known as organic extraction solvents and are well known to those skilled in the art. This known class of organic soluble complexing agents can be used alone or in solution in an organic solvent, normally a hydrocarbon solvent.

In another example, the thermodynamically-unstable complexing agent of the invention is used as a holdback reagent in a cobalt extraction/recovery process. Trivalent iron is a ubiquitous constituent in feed solutions for cobalt, nickel and copper recovery. Consequently, the trivalent iron must be either complexed or precipitated to prevent iron ion interference with the extraction process. The presently available complexing agents either do not function effectively at the acidities normally encountered in the feed stream or they create serious environmental and/or waste disposal problems. Generally, the iron ion is precipitated as a hydroxide but precipitation requires a tedious, costly and time-consuming solid-liquid separation. However, the thermodynamically-unstable complexing agent can selectively complex the iron ion and hold the iron ion in solution, therefore permitting the extraction of cobalt from nickel by standard procedures. The thermodynamically-unstable complexing agent then can be destroyed, thereby releasing the iron ion back into solution for a liquid-liquid separation, or for disposal, while precluding any environmental and waste disposal problems associated with the complexing agent originally used to complex the iron ion.

The thermodynamically-unstable agents of the present invention also can be used as a stripping agent for removing extracted metal ions from an organic extraction solvent, or as an extraction solvent cleanup reagent particularly in the fields of nuclear waste processing and nuclear fuel reprocessing. In this application, an aqueous solution of a thermodynamically-unstable complexing agent of the present invention is used to extract the metal ions from the organic extraction solvent such that the extraction solvent can be reused and the volume of waste material containing the metal ions can be reduced.

The ability of the thermodynamically-unstable complexing agents of the present invention to strongly complex with metal ions at pH values ranging from about 10 to pH values exhibited by 7 molar strong acids, combined with high aqueous solubility of metal ion complexes, improves the back-extraction efficiency, i.e., stripping efficiency, of the metal ion from the organic extraction solvent by the aqueous solution. In addition, the subsequent decomposition of the metal ion complex including the thermodynamically-unstable complexing agent, and of any free thermodynamically-unstable complexing agent, facilitates subsequent conversion of the metal ion to a more desirable chemical form, such as a glass formed by vitrification of a transuranic element fraction, for efficient disposal. Decomposition of the thermodynamically-unstable complexing agent results in products which do not interfere in forming the glass, or in storing a waste.

The thermodynamically-unstable complexing agents of the present invention, because of their unique ability to form metal complexes under highly acidic conditions, can be used in the purification of acids or highly acid solutions. One advantageous use is in the purification of phosphoric acid. Because phosphoric acid is normally commercially made from mined phosphate material (phosphate rock), it is usual that there are various metal ion contaminants present which end up in the phosphoric acid. These include contaminants such as iron and aluminum. To obtain high purity phosphoric acid from the impure aqueous mixture which results from the conversion of phosphate rock to phosphoric acid, several commercial processes utilizes an organic solvent to extract the phosphoric acid from the impure aqueous mixture. This leaves most of the metal ions and other impurities behind in the aqueous phase. The phosphoric acid can then be recovered from the organic solvent usually by distillation or back extraction with an aqueous medium.

Although substantially pure phosphoric acid is produced by these method, there is still a carryover of metal ions into the organic phase and when the organic solvent is removed, the metal ions remain in the purified phosphoric acid. This may or may not be a serious disadvantage depending on the end contaminant and on the use of the phosphoric acid. When it is used, for example, as food grade phosphoric acid, it is obviously advantageous if substantially all of the metal ions can be eliminated and especially the radioactive materials. The complexing agents of the present invention provide several methods by which this can be accomplished in a simple way using current commercial processing equipment.

The first method of use is to simply introduce the complexing agent into the impure phosphoric acid in order to act as a "hold back" agent for the metal ions. The complexing agent will act to complex the metal ions giving them higher affinity for the non-organic (or aqueous) phase, thereby having the effect of reducing the amount of metal ion impurities which pass over into the organic phase during the extraction. The remainder of the processing is the same as usual.

A second method, which is related to the first method, involves following the usual method of extraction and then extracting metal ions from the organic phase in an additional step. The first method described above has the advantage of not requiring additional equipment or an additional step. The second method requires a second extraction step which would normally be accomplished in a separate extraction column or mixing vessel. First the impure phosphoric acid is extracted with the organic solvent, as is usual, and then the organic solvent is in turn extracted with an aqueous solution of the complexing agent of the present invention.

In addition to being useful at low pH conditions, the complexing agents according to the present invention have a still further advantage which is their ease of decomposition either by allowing them to stand and autodecompose or, with mild heating or mild oxidizing conditions. Also, these methods will convert the complexing agent of the present invention into substantially non-noxious products which can be left in the food grade phosphoric acid or removed by simple methods such as being driven off by gentle heating. Furthermore, it is not expected that more than a small amount of the complexing agent of the present invention will pass into the organic phase.

As noted above, the complexing agents of the present invention are particularly useful for dealing with radioactive metals. This is due to the fact that the complexing agents are useful in high acid environments as well as the fact that the complex can be destroyed by degrading the complexing agent under mild conditions to inorganic compounds, thereby releasing the metal ion for easier concentration or disposal. Thus, handling of radioactive metal ions for disposal or for recovery is facilitated by use of the inventive complexing agents. Because of this property, the complexing agents can be used, advantageously, in a water solution to decontaminate the surfaces of equipment or reactors which have become contaminated with radioactive metal species contaminants. An aqueous solution of the inventive complexing agents (with or without additional surface active agents) can be used to wash the surfaces of contaminated equipment or to be pumped through a reactor to reduce radioactive contamination. To increase the effectiveness of the solution for decontamination purposes, the solution can be made acidic or an agent added to accelerate destruction or dissolution of the surface oxide layer which may be present on the contaminated metal surface. Solutions of the inventive complexing agent will be useful for removing contaminants which comprise the actinides, such as thorium, uranium, neptunium and americium and their radioactive decomposition products, including isotopes of molybdenum and zirconium. After use as a decontaminating agent, the solution of the complexing agent can be gently heated or allowed to stand or possibly heated with dilute oxidation agents under mild conditions to decompose the complexing agent and release the radioactive metal ions into aqueous solution which is substantially organic-free. This solution can then be treated by extraction or other means to further concentrate the radioactive metals for disposal or possible recovery. Recovering of the metals is also possible by precipitation of salts such as phosphate salts thereof. The aqueous medium can then be decanted or filtered from the precipitate.

When the inventive complexing agents are used under concentration and other conditions wherein a phosphate (or sulphur analog) salt precipitate is formed with the metal ions released by the decomposition of the complexing agent, the aqueous phase can easily be recycled. One need only provide a settling tank (or other separation means), remove the aqueous phase and reuse it by adding complexing agent.

In accordance with an important feature of the present invention, in screening compounds for their metal complexing ability, measurements were made on the degree of lowering of the distribution ratio, i.e., the ratio of metal ion concentration in the organic extraction solvent phase to metal ion concentration in the aqueous solution, of americium III, i.e., Am(III), or europium (III), i.e., Eu(III), in extractions from 0.1M $HNO_3$ and 0.01M $HNO_3$ using bis(2-ethylhexyl) phosphoric acid (HDEHP) as the organic extraction solvent. In addition, compounds were screened for their ability to readily decompose. Thermal degradation of the thermodynamically-unstable complexing agents was performed by heating the complexing agent in 8M $HNO_3$ at 100° C. The thermal degradation of the compounds were followed by analysis via $^1H$, $^{13}C$ and $^{31}P$ NMR (nuclear magnetic resonance) spectroscopy. Furthermore, the water-solubility of metal ion complexes formed with the inventive complexing agents was determined by using macroquantities of neodymium (III), i.e., Nd(III); thorium (IV), i.e., Th(IV), and uranium (VI), i.e., U(VI).

The compounds screened by the above procedures demonstrated that a suitable thermodynamically-unstable complexing agent has the general diphosphonic acid chemical structure depicted in structural formula (I):

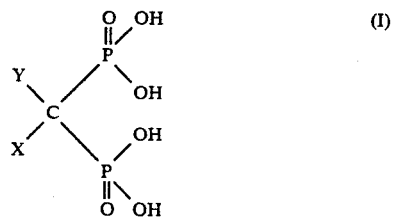

(I)

wherein the substituents X and Y are selected to adjust the susceptibility of the carbon-phosphorous bonds to oxidation and/or thermal degradation and/or autodecomposition. The substituents X and Y also are selected and varied to increase the acidity of the phosphonic acid groups in the molecule and to increase the water-solubility of the thermodynamically-unstable complexing agent and the metal ion complexes. Derivatives of compounds having structural formula I, such as monoesters, diesters and triesters, also demonstrate the thermodynamically-unstable complexing properties demonstrated by the parent compound of structural formula I.

Another class of disphosphonic acid compounds found to possess the desirable characteristics of a thermodynamically-unstable complexing agent are the substituted vinylidenediphosphonic acid, and its derivatives, as depicted in structural formula II.

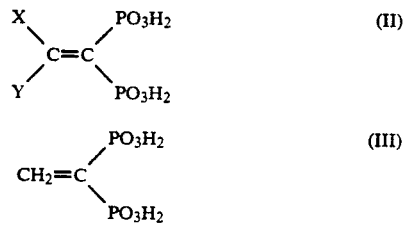

It further has been discovered that vinylidenediphosphonic acid (III) and its derivatives, such as a monoester, possess the water-solubility, the complexing ability and the thermodynamic decomposition properties to suitably perform as a thermodynamically-unstable complexing agent. Furthermore, it also is envisioned that condensed derivatives of the compound depicted in structural formula I, such as pyrolytic derivatives of compound I, like those depicted as general structural formulas IV, V and VI, also can be utilized as thermodynamically-unstable complexing agents in a liquid-liquid extraction method of the present invention.

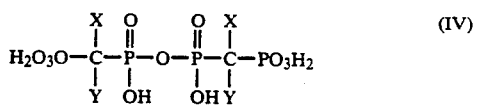

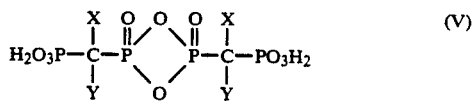

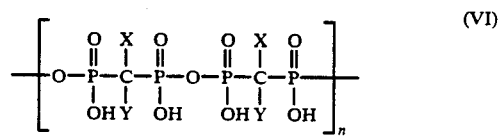

As previously stated, some diphosphonic acids that exhibit the desirable properties of a thermodynamically-unstable complexing agent and that have the structural formula I are known. However, several diphosphonic acids of structural formula I that exhibit the desirable properties of a thermodynamically-unstable complexing agent are new compounds, specifically designed to possess a moderate degree of thermodynamic instability. One example of a new, thermally-unstable complexing agent of structural formula I is the compound carboxyhydroxymethanediphosphonic acid, shown in structural formula VII, wherein the X substituent of structural formula I is a hydroxy functionality and, the Y substituent is a carboxy functionality.

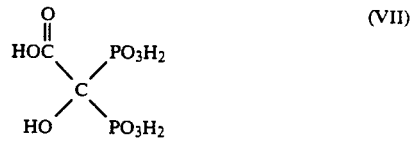

The disphosphonic acid compound of structural formula VII was prepared by a novel synthetic route including the reaction of methyl malonoyl chloride and triethylphosphite, $(C_2H_5O)_3P$, followed by reaction with diethylphosphite, $(C_2H_5O)_2HPO$. The resulting pentaethyl ester of VII then was converted to the free acid by de-esterification with trimethylsilyl iodide, $(CH_3)_3SiI$, to yield the diphosphonic acid compound VII. The diphosphonic acid compound VII demonstrated the acidity, water-solubility and metal ion complexing properties desired in a thermally-unstable complexing agent. In addition, the diphosphonic acid compound VII exhibited the moderate thermodynamic instability required in the thermodynamically-unstable complexing agent by autodecomposing to carbon dioxide, water and phosphoric acid. This autodecomposition of the free acid form of compound VII proceeded at room temperature with a half-life of from about two days to about three days. Consequently, the successful synthesis and isolation of compound VII demonstrated that diphosphonic acids of general structural formula I are suitable thermodynamically-unstable complexing agents in regard to water-solubility, complexing ability, and moderate thermodynamic instability.

It should be noted that, in general, the stability of an acid compound, such as compound VII, usually is increased by converting the free acid functionalities of the acid compound into a salt. Therefore, converting the acid form of compound VII into a salt retards or prevents autodecomposition of the product such that storage stability is increased. Then, converting the salt form of the compound VII back to the free acid form allows the user of the diphosphonic compound at least two to three days to use the compound before the compound autodecomposes. Such a compound lifetime is sufficient to perform the desired metal ion complexing in a liquid-liquid extraction process to separate metal ions from a waste stream.

Other diphosphonic acid compounds of structural formula I also demonstrate moderate thermal instability in the free acid form and excellent stability in the salt form. For example, the compound 1,2-dihydroxyethane-1,1-diphosphonic acid, corresponding to the compound of structural formula I wherein the X substituent is a hydroxymethylene functionality and the Y substituent is a hydroxy functionality, is stable indefinitely in the sodium salt form. However, in the free acid form, 1,2-dihydroxyethane-1,1-diphosphonic acid decomposes to water, carbon dioxide and phosphoric acid either by autodecomposition at room temperature with a half-life of about 15 days, or totally decomposes in about 3 hours in boiling 8M $HNO_3$ or in the presence of hydrogen peroxide at about 60° C.

Similarly, another thermodynamically-unstable complexing agent of the present invention, vinylidenediphosphonic acid (III) is stable in both the free acid and the salt form, but decomposes within hours in boiling nitric acid or by aqueous hydrogen peroxide at moderately elevated temperatures. It also should be noted that vinylidenediphosphonic acid (III) after complexing with a metal ion can be decomposed by salts of vanadium(V) under very mild conditions. This facile decomposition demonstrates that, after metal complexation, the thermally-unstable complexing agents are further reduced in thermodynamic stability, such that complexing agent decomposition is achieved under more mild conditions. As a result, autodecomposition is observed when the thermodynamically-unstable complexing agents of the present invention complex with metal ions such as ruthenium or tungsten.

Therefore, to increase the thermodynamic stability of a compound of general structure I, the substituents X and Y are selected such that the diphosphonic acid compound still can autodecompose, but over a longer half life, or such that the diphosphonic acid compound is stable at ambient and slightly elevated temperatures, such as the temperatures encountered during manufacture and during the liquid-liquid extraction process but that decomposes upon moderately increased temperatures, such as from about 60° C. to about 100° C., and/or in the presence of mild oxidizing agents, like hydrogen peroxide or nitric acid. The preferred salts for stabilizing the complexing agents of the present invention are the sodium and potassium salts.

In providing other diphosphonic acid compounds of structural formula I that demonstrate thermodynamically-unstable complexing agent properties, it was discovered that an important intermediate in the preparation of compounds of structural formula I is the vinylidene-1,1-diphosphonic acid compound (II). Vinylidene-1,1-diphosphonic acid (III) is a thermodynamically-unstable complexing agent and is also useful as an intermediate compound in a synthetic scheme that provides a variety of disphosphonic acid compounds demonstrating the desirable properties of a thermodynamically-unstable complexing agent. The prior art teachs that the substituted vinylidene-1,1-diphosphonic acid (II) can be converted into a variety of $\alpha,\beta$-substituted ethanediphosphonic acids via an intermediate epoxide with a nucleophilic compound. In particular, the intermediate epoxide can be opened with a nucleophilic compound of formula HA, corresponding to, but not limited to, such nucleophilic compounds as water, hydrochloric acid (HCl), hydrobromic acid (HBr), hydriodic acid (HI), hydrofluoric acid (HF), nitrous acid ($HNO_2$), hydrogen cyanide (HCN), ammonia alcohols (ROH), amines ($RNH_2$ and $R_2NH$), hydrogen sulfide ($H_2S$) and mercaptans (RSH), wherein R is an alkyl group including from one to three carbon atoms, to provide thermodynamically-unstable complexing agents of the formula:

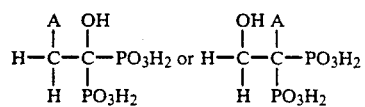

Therefore, a more efficient method than the method disclosed in the prior art of manufacturing and purifying vinylidenediphosphonic acid was sought. Accordingly, it was found that vinylidenediphosphonic acid (III) can be prepared by the dehydration of the commercially available compound 1-hydroxyethane-1,1-diphosphonic acid (VIII).

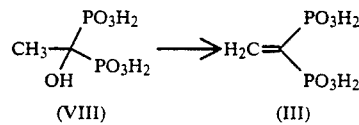

Subsequent oxidation of III with hydrogen peroxide plus a catalytic amount sodium tungstate gave the 1,2-dihydroxyethane-1,1-diphosphonic acid (X) presumably via the epoxide (IX). All attempts to isolate the epoxide IX failed because the epoxide IX is unstable under these reaction conditions.

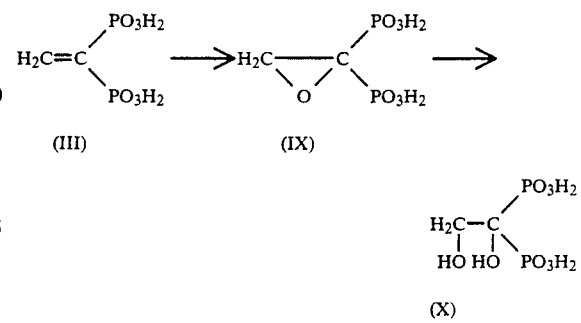

In addition, in contrast to the results disclosed in the prior art patents describing the dihydroxy compound X, the dihydroxy compound X was not stable but autodecomposed at ambient temperature with a half-life of about 15 days.

It was discovered that both diphosphonic acid compound III and disphosphonic acid compound X demonstrated each of the properties desired in a thermally-unstable complexing agent. Although diphosphonic acid compound VIII demonstrated an excellent ability to complex with metal ions in acidic media, compound VIII resisted degradation under mild thermal and/or oxidation conditions. In addition, complexes formed between the diphosphonic acid compound VIII and neodymium (III), and complexes formed between compound VIII and thorium (IV), demonstrated only moderate aqueous solubilities in acid media. Accordingly, the diphosphonic acid compound VIII is unsuitable as a thermally-unstable complexing agent of the present invention in a liquid-liquid extraction method to separate and remove metal ions from acidic media.

To further demonstrate the usefulness of the diphosphonic acid compound X as thermodynamically-unstable complexing agent in a liquid-liquid extraction method to separate and remove metal ions from acidic media, it was found that the tetrasodium salt of compound X is stable indefinitely at room temperature whereas the free acid form of compound X autodecomposes to phosphorous and phosphoric acids with a half-life of about 15 days. Therefore, the stability of compound X is improved over diphosphonic acid compound VII and allows the user of compound X to indefinitely store compound X in its salt form, then convert the salt form of compound X to the free acid form. The user therefore still has several days to use the thermodynamically-unstable complexing agent X in an extraction process before the compound X autodecomposes into environmentally-nondamaging compounds. It has been proposed that the decomposition of diphosphonic acid compound X occurs via the following degradation pathway:

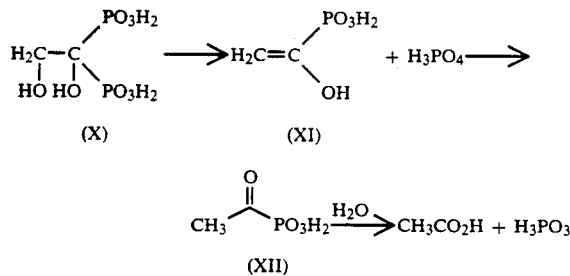

In regard to compound III, it was demonstrated that vinylidenediphosphonic acid is stable both in its free acid form and in its sodium salt form. Furthermore, vinylidenediphosphonic acid (III) forms very soluble metal ion complexes in acidic media and is readily decomposed by metal catalyzed oxidation with hydrogen peroxide. Therefore, similar to compound X, compound III demonstrates excellent ability to act as a thermodynamically-unstable complexing agent in a liquid-liquid extraction method of separating and removing metal ions from aqueous solutions.

In addition to diphosphonic acid compounds III, VII and X, other diphosphonic acid compounds of structural formula I possess the unique combination of properties that make the compound suitable as a thermodynamically-unstable complexing agent. Various compounds having structural formula I were synthesized and/or analyzed for having the ability to form highly stable, water-soluble complexes with metal ions, including metal ions in the III, IV, V and VI oxidation states, in from moderately alkaline to highly acidic solutions, such as 0.1M $HNO_3$ for 3+ ions and 7M $HNO_3$ for 4+ ions, and, also for having the ability readily decompose to environmentally-nondamaging substances, such as carbon dioxide, water and phosphoric acid, either by autodecomposition and/or upon heating to moderately elevated temperatures and/or in the presence of mild oxidizing agents. The following Examples 1-8 in TABLE I show some diphosphonic acid compounds of structural formula I that demonstrated, or are expected to demonstrate, the advantageous properties, of a thermodynamically-unstable complexing agent:

TABLE I

Compounds of Structural Formula I Demonstrating Suitable Properties for Use as a Thermally Unstable Complexing Agent

| Example | Substituent X | Substituent Y |
| --- | --- | --- |
| 1 | OH | $CO_2H$ |
| 2 | OH | $CH_2OH$ |
| 3 | OH | $CH_3$ |
| 4 | H | $CH_2OH$ |
| 5 | OH | $CH_2NH_2$ |
| 6 | OH | $CH_2Cl$ |
| 7 | OH | $CH_2NO_2$ |
| 8 | OH | H |

It should be understood that the above Examples are merely illustrative, and are by no means exhaustive of diphosphonic acids and diphosphonic acid derivatives that posses the unique and desirable properties of a thermally-unstable complexing agent.

In general, thermodynamically-unstable complexing agents of the present invention include substituted vinylidenediphosphonic acids (II) and diphosphonic acid compounds of structural formula I that demonstrate the ability to complex with metal ions in moderately alkaline to highly acidic media to form water-soluble complexes and the ability to degrade to environmentally-nondamaging compounds under mild conditions. Accordingly, in addition to the combinations of X and Y substituents listed in TABLE I, the substituents X and Y of the compound of structural formulas I and II can be identical or can be different, and each of the substituents X and Y can be independently selected from the representative group of substituents including —H, —OH, —$CO_2H$, —$CH_2OH$, —$CH_3$, —$CH_3$, —$CH_2CH_3$, —$CH_2NH_2$, —$CONH_2$, —$CH_2Cl$, —$CH_2Be$, —$CH_2Fl$, —$CH_2I$, —$CH_2NO_2$, —$CH_2CN$, —$CH_2OR$, —$CH_2SR$,

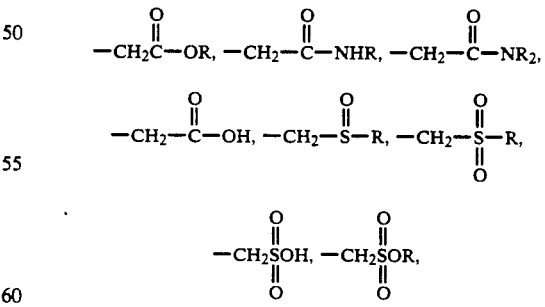

—$CH_2$—$PO(OH)_2$, and —$CH(PO_3H_2)_2$, wherein R is an alkyl group including from one to three carbon atoms. It should be understood that the preceding list of substituents is merely illustrative of the possible X and Y substituents of a compound of structural formula I, and that the preceding list is not limiting and is not exhaustive of all possibilities for substituents X and Y.

In addition, a diphosphonic acid compound of structural formulas I and II can be converted into a derivative of the diphosphonic acid, such as like being esterified, or thioesterified, either at a phosphonic acid group or at a carboxyl group, if present, with an alcohol, or a mercaptan, containing from one carbon atom to about four carbon atoms. The degree of esterification or thioesterification, such as monoesterification, diesterification or triesterification, can proceed up to any level provided that the diphosphonic acid or diphosphonic acid derivatives of structural formulas I and II retains their water-solubility in the metal complexed state and in the uncomplexed state; can effectively complex with metal ions, including metal ions of oxidation states II, III, IV, V and VI, in moderately alkaline to highly acidic media; and is autodecomposed and/or is readily decomposed at moderately increased temperatures and/or in the presence of mild oxidizing agents. In addition, the thioderivatives of compounds of structural formulas I and II, the dithiophosphonic acids, such as the thioderivatives of the thermally-unstable complexing agent of Example 2 and of vinylidenediphosphonic acid (III) as depicted in structural formulas XIII and XIV, respectively, also can be used in the method of the present invention, as can various derivatives of these dithiophosphonic acids, such as esters and thioesters.

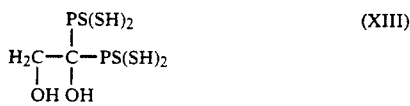
(XIII)

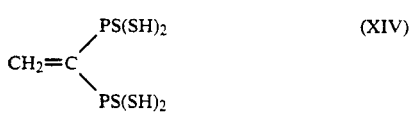
(XIV)

Some of the thermodynamically-unstable complexing agents of the present invention are known compounds, and some of the thermodynamically-unstable complexing agents of the present invention are new compounds. For example, vinylidenediphosphonic acid (III) is known. Vinylidenediphosphonic acid, however, is useful as a thermally-unstable complexing agent in a liquid-liquid extraction method of separating and removing metal ions from solution. Similarly, the compound of Example 2 (X), 1,2-dihydroxyethane-1,1-diphosphonic acid, was described in the prior art. Furthermore, the compounds of Examples 2, 5, 6 and 7 are synthesized from vinylidenediphosphonic acid by forming the epoxide of structural formula XV, followed by the nucleophilic addition of water, ammonia, chloride ion and nitrite ion, respectively.

(XV)

In accordance with an important feature of the present invention, a novel method of preparing vinylidenediphosphonic acid (III) and 1,2-dihydroxyethane-1,1-diphosphonic acid (X) was discovered. The prior art methods of manufacturing these compounds led to insufficiently pure vinylidenediphosphonic acid. Therefore, the vinylidenediphosphonic acid was unsuitable for subsequent reactions to provide diphosphonic acid compounds of structural formula I. Therefore, Examples 9 and 10 demonstrate the novel methods of preparing pure vinylidenediphosphonic acid (III) and of preparing the thermally-unstable dihydroxyethanediphosphonic acid complexing agent (X).

EXAMPLE

Preparation of Vinylidenediphosphonic Acid (VDPA) (III)

1-hydroxyethane-1,1-diphosphonic acid (HEDPA) (VIII) (70% aqueous solution) first is purified by crystallization from an acetic acid solution prepared by adding 3 parts volume of glacial acetic acid to 1 part HEDPA solution.

The tetrasodium salt of HEDPA then is prepared by adding 4 equivalents of 1M sodium hydroxide (NaOH) to the purified HEDPA in water. After stirring for 30 minutes, the aqueous solvent is removed in vacuo at 50° C. to provide the solid tetra-sodium salt of HEDPA.

The tetrasodium salt of HEDPA hydrate (240 g) then is introduced into a 6.5 cm×75 cm glass tube in two batches. The glass tube is attached to a rotary motor that is set to rotate the tube at the rate of 5 revolutions per minute. A condenser and vacuum attachment then are connected to the rotary motor. After establishing a vacuum of approximately 25 torr, the tube then is inserted into a 3 inch tube furnace. The temperature is raised to about 400° C., and the tube is maintained at that temperature for 3 hours. After cooling the tube to room temperature, the resulting tan-colored solid (180 g), including 60% by weight of VDPA is dissolved in 330 mL of water at 95° C. Methanol is added slowly until the hot aqueous solution becomes turbid. Heating is maintained until the aqueous solution again becomes clear. The warm solution then is covered and, undisturbed, allowed to cool slowly to room temperature. The resulting white solid is isolated by filtration to provide 185.5 g of a tetrasodium salt of VDPA. The VDPA salt is greater than 95% pure as demonstrated by $^1$H NMR, $^{31}$P NMR, and ion chromatography.

EXAMPLE

Preparation of 1,1-Dihydroxyethane-1,1-diphosphonic Acid (DHEDPA) (X)

A solution containing 36.7 g of the tetrasodium salt of VDPA (II) in 100 mL of water is passed slowly through a column containing 133 g of BIORAD AG MP-50, an acidic ion exchange resin available commercially from BioRad. After the column is loaded, an additional 100 mL of water then is introduced in order to completely elute the acidic form of VDPA. The resulting solution is charged with 1.6 g of sodium tungstate and 54 mL of 30% hydrogen peroxide, then the solution is warmed to 60° C. for 3 hours. After cooling to room temperature, the DHEDPA product (X) is isolated in one of two ways:

Method A: Dilute aqueous sodium hydroxide (NaOH) is added dropwise to the above cooled solution until a pH of 6.2 is attained. The aqueous solvent then is concentrated in vacuo to provide a white syrup-like material. Approximately 50 mL of acetone is introduced and the resulting mixture is mechanically stirred for about one hour. The acetone solvent is decanted and another 50 mL of fresh acetone is introduced into the mixture. After again decanting the acetone solvent, the DHEDPA product (25 g, 90% yield, 85% pure) is dried in vacuo at 50° C. overnight. The DHEDPA product (IX) was identified by $^1$H NMR and $^{31}$P NMR. The 15% impurity present consisted of sodium phosphate and sodium pyrophosphate.

Method B: Sodium carbonate (22.2 g) is introduced slowly to the above solution with stirring. The solution volume is reduced by approximately one-half using a rotary evaporator at room temperature. Acetone (200 mL) is introduced into the solution, and the resulting mixture then is stirred for about one hour. The acetone solvent is decanted, then the procedure is repeated. The resulting white solid was dried in vacuo at 50° C. to provide the DHEDPA compound (X) in 90% yield.

It should be noted that previous attempts to isolate DHEDPA (X) in its free acid form, as taught by the prior art patent references, resulted in the essentially immediate conversion of the diphosphonic acid product (X) to phosphoric acid. In contrast, and in accordance with an important feature of the present invention, the present ability to synthesize the free acid form of DHEDPA is new and totally unexpected.

Furthermore, in addition to the sodium tungstate, other catalytic metal oxides, such as oxides of molybdenum(VI) and vanadium(V), can be used to catalyze the reaction of Example 10. Also, any hydroperoxide or peroxycarboxylic acid, in addition to hydrogen peroxide, can be used to oxidize a vinylidenediphosphonic acid of structure II. Such hydroperoxides include cumene hydroperoxide, t-butyl hydroperoxide, peroxyacetic acid, and peroxybenzoic acid.

The manufacture of other diphosphonic acid compounds of structural formula I can be accomplished by other synthetic methods. For example, the preparation of the compound of Example 4 of TABLE I, i.e., the disphosphonic acid compound of structural formula XVII, can be achieved by the condensation of the sodium salt of tetraethylmethylenediphosphonate (XVI) with gaseous formaldehyde,

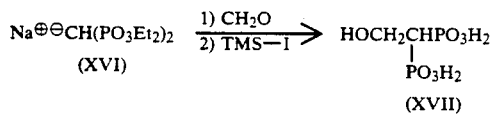

followed by de-esterification using trimethylsilyl iodide. The anion XVI can be prepared according to prior art literature procedures from dibromomethane by using Arbusov chemistry. In addition, the above reaction sequence can be used in the condensation between XV and various other aldehydes, in addition to formaldehyde, thereby providing additional diphosphonic acid compounds of structural formula I, such as the ethylenically unsaturated diphosphonic acid XVIII and the epoxidized diphosphonic acid XIX as depicted below:

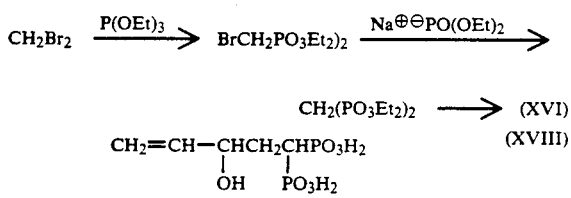

-continued

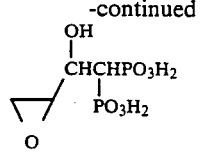

Similarly, the diphosphonic acid of Example 8 in TABLE I, hydroxymethanediphosphonic acid, shown as structural formula XX, can be prepared by an Arbusov reaction between triethylphosphite and phosgene, followed by reduction of the intermediate compound with a suitable borohydride reagent and finally by deesterification with trimethylsilyl iodide.

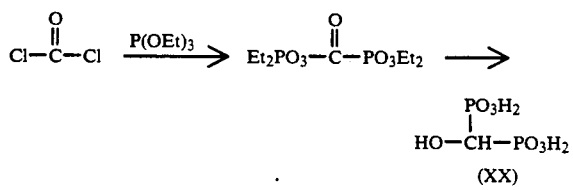

After synthesis, the thermodynamically-unstable complexing agents of the present invention were tested for thermal stability and susceptibility to oxidation by using $^1H$, $^{13}C$ and $^{31}P$ NMR spectroscopy. Furthermore, the acid dissociation constants, i.e., the $pK_a$ values, of the thermodynamically-unstable complexing agents were determined by standard potentiometric titration methods. Finally, the thermodynamically-unstable diphosphonic acid complexing agents of the present invention were analyzed with respect to their ability to complex metal ions and with respect to the aqueous solubility of the resulting metal ion complexes. In addition, the solubility of the uncomplexed thermodynamically-unstable complexing agents was determined by using macro-concentrations of neodymium-(III) as a substitute for the trivalent actinides; of thorium(IV), as a substitute for plutonium(IV) and neptunium(IV); of uranyl(VI), as representative for all actinide(VI) ions; of iron(III); and of zirconium. The variables included in this solubility determination were the thermally-unstable complexing agent-to-metal ion ratio, the metal ion concentration, and the pH.

In addition, the results of the oxidative degradation determinations, the $pK_a$ determinations and the solubility measurements were used to select particular thermally-unstable complexing agents for determination of metal ion complexation equilibria. Representative actinides in the III, IV, V and VI oxidation states, or their lanthanide substitutes, were used in these equilibria studies because these ions attain equilibrium rapidly and are less prone to interferences due to hydrolysis reactions than the polyvalent transition metals. In addition, complexation studies on nonactinide and nonlanthanide metal ions also were performed.

More particularly, $^1H$, $^{13}C$, and $^{31}P$ NMR spectroscopy was used to elucidate and measure the thermal degradation pathways of the thermally-unstable complexing agents of structural formula I, and to evaluate synthesis efforts. For example, $^{31}P$ NMR spectroscopy is especially valuable in identifying the type of phosphorus compound that is synthesized or the type of phosphorous compound produced upon degradation of the thermally-unstable complexing agent. As a result, $^{31}P$ NMR spectroscopy provides a method of showing that a particular diphosphonic acid compound actually was synthesized. TABLE II demonstrates the sensitivity of the $^{31}P$ NMR chemical shifts resulting from the chemical environment surrounding the phosphorus atom.

TABLE II $^{31}P$ NMR Chemical Shifts of Various Phosphorous-Containing Compounds and Various Diphosphonic Acids (0.2 M $D_2O$)

| Compound | ppm (85% $H_3PO_4$) |
|---|---|
| Phosphoric Acid | 3.10 |
| Phosphorous Acid | 4.50 |
| 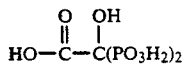 HO—C(=O)—C(OH)(PO$_3$H$_2$)$_2$ | 7.50 |
| 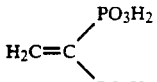 H$_2$C=C(PO$_3$H$_2$)$_2$ | 12.11 |
| 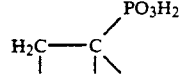 H$_2$C(OH)—C(OH)(PO$_3$H$_2$)$_2$ | 13.59 |
| 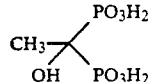 CH$_3$—C(OH)(PO$_3$H$_2$)$_2$ | 20.43 |

In addition, the thermodynamics of protonation of the thermodynamically-unstable complexing agents of the present invention was investigated by potentiometric (pH) titration.

The acidity constants of the thermodynamically-unstable complexing agents are important in the interpretation of metal ion complexation studies, and also serve as a preliminary indicator of metal ion complex stability and conformation. TABLE III summarizes the acid dissocation constants ($pK_a$) of three substituted diphosphonic acids of the present invention. The acid dissociation constants of oxalic and phosphoric acids are included for comparison.

TABLE III

Acidity Constants of Substituted Diphosphonic Acids
Ionic Strength = 2M (NaNO$_3$)

| | $pK_1$ | $pK_2$ | $pK_3$ | $pK_4$ |
|---|---|---|---|---|
| Oxalic Acid* | 1.04 | 3.55 | — | — |
| Phosphoric Acid* | 1.70 | 6.46 | 10.80 | — |
| HEDPA (XIII) | 1.53 | 2.16 | 6.18 | 9.09 |
| VDPA (III) | 1.41 | 2.05 | 5.98 | 8.58 |
| DHEDPA (X) | 0.91 | 1.59 | 5.82 | 7.97 |

*pKa's are at 1M ionic strength

The data in TABLE III demonstrates that the thermodynamically-unstable diphosphonic acids of the present invention are strong acids, particularly DHEDPA, the compound of structural formula (X). Low acid dissociation constants are important for a thermally-unstable complexing agent of the present invention in order for the compound to act as an effective metal ion complexing agent at low pH values. It also should be noted that the data in TABLE III shows that the electron withdrawing effect of a 1-hydroxyl group in HEDPA and the vinylidene group in VDPA are essentially equivalent, whereas the 1,2-dihydroxy functionality in DHEDPA produces the strongest acid. Also noteworthy is the large difference between the $pK_2$ of oxalic acid and phosphoric acid and the $pK_2$ values for each of the diphosphonic acids of the present invention. Theoretically this large difference is due in part to the greater charge separation in the dianions of the diphosphonic acids.

Metal ion complexation with the thermodynamically-unstable complexing agent was investigated using the solvent extraction distribution ratio method. The medium used in all of the protonation and complexation studies was 2.0M NaNO$_3$/HNO$_3$. The relatively high ionic strength of this medium was utilized in order to minimize interferences due to activity coefficient changes. Data interpretation in all experiments was accomplished by the application of a generic least-squares program written in BASIC. The program applies a Newton-Raphson type iterative process to the data and minimizes the sum of squares of the residuals. The generic program was adapted to several different forms to fit distribution ratio lowering (Do/D) vs. free ligand concentration measurements, and $\bar{p}$ (average proton number) data from potentiometric titrations.

Also, in particular, the determination of the stability constants for the rare earth and actinide ion complexes with the thermodynamically-unstable complexing agents is accomplished by one of two means, depending upon the specific metal ion being complexed. For non-radioactive, or low specific activity, metal ions, such as the rare earths, thorium and uranium, stability constants are determined by conventional potentiometric titration techniques combined with a least-squares computer analysis. Such an approach entails performing acid-base titrations of mixtures of the metal ion and the thermodynamically-unstable complexing agent. The titrations are performed under variable conditions, such as varying the metal-to-ligand ratio and the total metal ion concentration, to permit a precise definition of all pertinent equilibrium constants.

The thermodynamically-unstable complexing agents are polybasic acids, therefore a variety of protonated complexed species of the general from $MH_hL_l$, wherein M is the metal ion, H is hydrogen ions, h is the number of hydrogen ions, L is the thermodynamically-unstable complexing agent and l is the number of the thermodynamically-unstable complexing agents, are expected. The computer model used to fit plots of the average ligand number $\bar{n}$ vs. pH requires that the combination of parameters describing various complexation equilibria achieve a unique solution to the titration data and minimize the residuals of the least-squares fit. Due to the nature of the thermodynamically-unstable complexing agent compounds, it is expected that the fitting procedure requires from 2 to 6 parameters (stability constants). In addition, if feasible, the titrations were performed at more than one ionic strength to permit extrapolation to infinite dilution in order to determine thermodynamic stability constants.

The above-described titration method also can be applied to the determination of the Am(III) and the Pu(IV) stability constants as well. However, since these metal ions have no stable isotopes, the titration technique required a glove-box operation and special shielding. The experimental method of choice for Am and Pu is to determine the influence of the complexing agent on the distribution ratio obtained with selected liquid-liquid extractant systems. For example, the $D_{Am}$ or $D_{Pu}$ distribution ratio is measured using the extraction solvent bis(2-ethylhexyl) phosphoric acid (HDEHP) as a function of the concentration of the complexing ligand in the aqueous phases at varying pH. As the concentration of the complexing agent increases, the distribution ratio decreases. The decline in the distribution ratio is related mathematically to the concentration of the complexing agent, and the stability constants of the complexes are determined by least-squares fitting procedures. The polybasic nature of the thermodynamically-unstable complexing agents requires that a variety of distribution ratio experiments be performed as a function of both complexing agent concentration and pH to adequately define the nature of the metal ion complexes.

Therefore, since the thermodynamically-unstable complexing agents of the present invention are polybasic acids, it is theorized that they will form a variety of complexes of the form, $MH_hL_l$. Consequently, the relative complexing ability of a series of thermally-unstable complexing agents can be compared by measuring the distribution ratio of a metal ion, e.g., Am(III) or Eu(III), using bis(2-ethylhexyl)phosphoric acid (HDEHP) as a function of the concentration of the complexing agent ligand in aqueous phases and of varying pH. Assuming reversible extraction and complexation equilibria, the following series of equations demonstrate the effect of aqueous complexation on distribution ratios. If the distribution ratio is written as:

$$D = [M]_{org}/[M]_{aq},$$

wherein $[M]_{org}$ is the metal ion concentration in the organic phase and $[M]_{aq}$ is the metal ion concentration in the aqueous phase, a distribution ratio for the metal ion in the presence and absence of the aqueous chelating agent can be defined as:

$$D_o = [M]_{org}/[M^{3+}] \text{ and}$$
$$D = [M]_{org}/[M^{3+}] + \Sigma[MH_hL_1],$$

wherein $[M^{3+}]$ is the concentration of $M^{+3}$ ion in aqueous solution and $\Sigma[MH_hL_1]$ is the sum of the concentrations of the metal ion complexes and where $MH_hL_1$ are mononuclear protonated complexes of the metal ion with the complexing agent. Assuming that the metal ion complexes $MH_hL_1$ are not extracted into the organic phase, a "stripping factor", $[(D_o/D)-1]$, is defined that measures the ability of the complexing agent to remove, or retain, the metal ion in the aqueous phase. The stripping factor is a measure of the amount that distribution ratios are reduced under the conditions pertaining in the aqueous phase. Generally the stripping factor applies equally to neutral and acidic extractants.

FIG. 1 shows a plot of the stripping factor $[(D_o/D)-1]$ vs. the total complexing agent concentration. The hydrogen ion concentration of all aqueous phases was 0.1M. The calculated data for oxalic acid was included in FIG. 1 for comparison because oxalic acid is presently regarded as a very effective stripping agent. However, oxalic acid usually is limited to tracer scale metal ion concentrations because of the low solubility of many oxalate complexes. Data for HEDPA (VIII) also is included to show that HEDPA is an excellent complexing agent in acidic media. However, HEDPA is not a thermodynamically-unstable complexing agent because of its ability to resist decomposition.

Surprisingly and unexpectedly, the data presented in FIG. 1 show that at a given complexing agent concentration, each of the diphosphonic acids of the present invention outperformed oxalic acid by a substantial amount. The differences between oxalic acid and the diphosphonic acids of the present invention vary as the acidity of the aqueous phase changes. In accordance with another important feature of the present invention, FIG. 1 demonstrates that higher acidities of the complexing agent having the lowest acid dissociation constants enhance the relative complexing effectiveness.

From the data presented in FIG. 1, and from additional data found down to $[H^+]=0.02M$ (hydrogen ion concentration) the following aqueous equilibria were derived, wherein M is Eu:

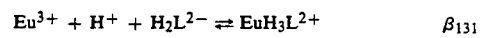
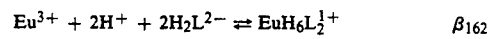
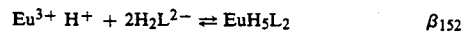
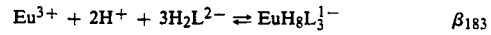

wherein $\beta_{Mhl} = \dfrac{[EuH_hL_2]}{[Eu][H^+]^{h-2l}[H_2L^{2-}]^l}$.

The derived equilibrium coefficients are presented in TABLE IV, wherein it is noted that four equilibria are required to fit the Eu-VDPA data whereas five equilibria are necessary to fit the Eu-HEDPA data.

TABLE IV

| | | log³ Mhl | |
| Equilibria | Complex | Eu-VDPA | Eu-HEDPA |
| --- | --- | --- | --- |
| β 131 | EuH₃L²⁺ | 5.71 | 6.43 |
| β 121 | EuH₂L¹⁺ | 3.70 | 4.58 |
| β 162 | EuH₆L₂¹⁺ | 9.96 | 11.47 |
| β 152 | EuH₅L₂ | — | 9.76 |
| β 142 | EuH₄L₂¹⁻ | 6.33 | — |
| β 183 | EuH₈L₃¹⁻ | — | 14.56 |

Therefore, for the Eu-HEDPA system, 1:3 complexes, i.e., the stoichiometric ratio of metal to complexing agent found in the metal ion complex, are observed, whereas for VDPA, the metal to complexing agent stoichiometry apparently does not exceed 1:2. Europium ion complex species of the proper stoichiometry are formulated by assuming monodentate, bidentate, and mixed mono and bidentate coordination as shown below in structural formulas XXI through XIV:

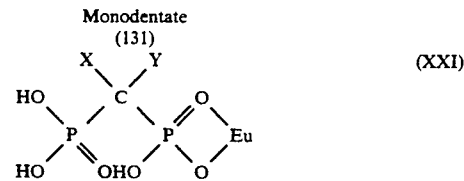

(XXI)

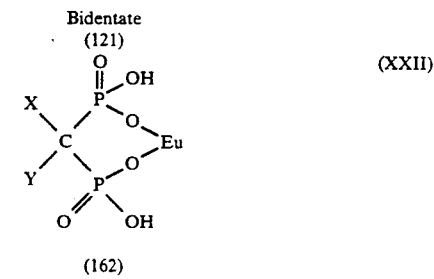

(XXII)

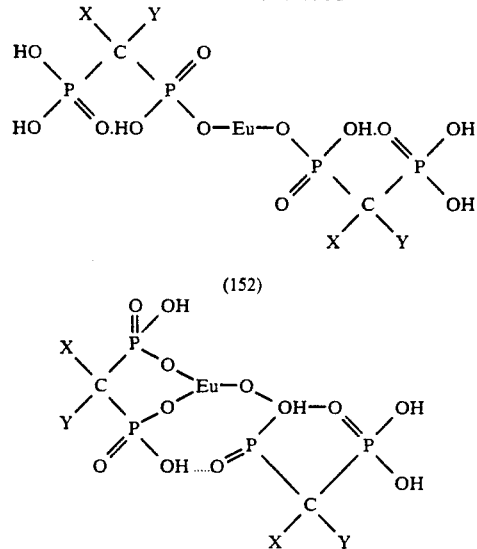

as a holdback complexant can be applied in the hydrometallurgical processing of cobalt and nickel. The thermodynamically-unstable complexing agent is used to complex any iron ion and zinc ion interferants in acidic media, thereby permitting the extraction of $Co^{2+}$ (cobalt) and $Ni^{2+}$ (nickel) at very low pH values. In each of the above examples, the use of a thermodynamically-unstable complexing agent considerably diminishes the demands placed on the selectivity of the extraction solvent used in the extraction system.

It also is envisioned that other diphosphonic acid derivatives having lower acid dissociation constants and forming more stable complexes than the diphosphonic acids and diphosphonic acid derivatives described above can serve as thermodynamically-unstable complexing agents. Such compounds include the mono- and dipyrodiphosphonic acids. Examples are bis-[methylenepyrodiphosphonic acid] (IV) and bis-[methylenedipyrodiphosphonic acid] (V).

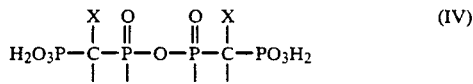

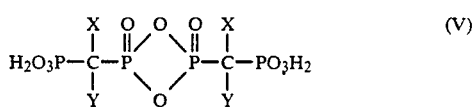

It is further envisioned that compounds IV and V can be made by heating the trisodium and disodium salts of methanediphosphonic acid (XXV), respectively, to approximately 300° to 400° C. in a vacuum to provide compound IV or compound V.

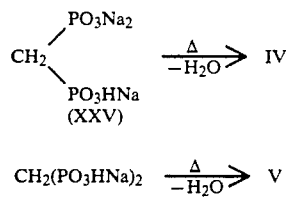

$$CH_2(PO_3HNa)_2 \xrightarrow[-H_2O]{\Delta} V$$

Theoretically, the inductive effect of the pyro-oxygen and the separation of the phosphonic acid groups would substantially lower $pK_1$ and $pK_2$ (i.e., increase acidity) in compound IV.

Compound IV also can form very stable complexes through the pyrophosphonic acid groups. Compound V has a less favorable structure for metal ion complexation and its preparation by pyrochemical means could possibly lead to some polymer formation (XXVI) in addition to compound V.

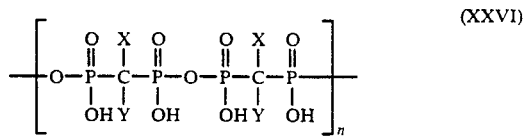

The ability of both compound XXV and XXVI to perform as thermodynamically-unstable complexing agent could be enhanced further by placing a hydroxyl substituent on the methylene carbon. Hydroxyl-substituted IV and V can be prepared pyrochemically from the The thermodynamically-unstable complexing agents of the present invention can be used in nuclear waste processing, by-product recovery from nuclear waste, the processing of waste brine solutions from oil recovery and in hydrometallurgical processing. An important aspect in utilizing the thermodynamically-unstable complexing agents in these applications is to predict how closely the behavior of a thermodynamically-unstable complexing agent of the present invention as a holdback and stripping reagent correlates to the acid dissociation constants and the metal ion stability constants of the thermodynamically-unstable complexing agent. Such a correlation is important because normally it is not possible to verify experimentally all the possible conditions wherein a thermodynamically-unstable complexing agent can be utilized.

For example, the thermodynamically-unstable complexing agents of the present invention can be tested for their ability to enhance the back-extraction (stripping) of all actinides from the extraction solvent used in a liquid-liquid extraction method of treating an acidic waste stream from a nuclear facility. The use of a thermodynamically-unstable complexing agent can provide a significant improvement in the efficiency of the process, especially if the wastes are to be vitrified. The thermodynamically-unstable complexing agents of the present invention improve such methods because they are environmentally safe due to facile decomposition to innocuous compounds, therefore no additional and difficult to process waste streams are generated; they operate at very acidic pH ranges thereby avoiding dilution of the waste stream; and they effectively concentrate the waste stream.

Another potential application of the thermodynamically-unstable complexing agents of the present invention is in the extraction of $^{90}Sr$ (strontium) and $^{137}Cs$ (cesium) from acidic high-level waste solutions. A thermodynamically-unstable complexing agent can be used to complex the polyvalent metal ions in 2M to 3M $HNO_3$, therefore significantly improving the selectivity of crown ether extractants for strontium and cesium ions, or the selectivity of strongly acidic organophosphorus extractants for strontium. As previously discussed, the same selectivity enhancement principle of using a thermodynamically-unstable complexing agent appropriate sodium salts of hydroxymethanediphosphonic acid.

In accordance with an important feature of the present invention, a class of water-soluble, thermodynamically-unstable complexing agents were developed, that when introduced into a feed stream containing a variety of metal ion species improves the selectivity of an organic extraction solvent in a liquid-liquid extraction process for a particular metal ion species over the remaining metal ion species. Furthermore, the thermodynamically-unstable complexing agents of the present invention are environmentally safe materials because they are decomposed either by autodegradation or under mild thermal or oxidation conditions to innocuous materials, such as water, carbon dioxide and phosphoric acid. The thermodynamically-unstable complexing agents of the present invention have wide application in solvent extraction of metal ions and in hydrometallurgy.

Therefore, the present invention allows treatment of chemical solutions, such as aqueous nuclear waste, aqueous feed solution for hydrometallurgical processing, and waste brine solutions from oil recovery, with thermodynamically-unstable complexing agents to suppress a particular metal ion or metal ions from interfering with the normal processing operations on the solution. In particular, the present invention relates to using complexing agents that are stable at normal processing temperatures, but are unstable at moderately elevated temperatures to effect decomposition of the metal ion complex at a predetermined stage in the process.

Accordingly, the thermodynamically-unstable complexing agents of the present invention are used in treatment operations to form metal complexes with a particular metal ion species in an industrial solution. Therefore, the desired processing operations can be continued with the metal ion complex being readily degradable under mild conditions at a later stage of the process to release the particular complexed metal ion species back into the industrial solution for eventual recovery or disposal.

Consequently, the present invention allows the treatment of a solution containing at least one metal ion that interferes with the processing of the solution. The treatment involves forming of a water-soluble complex between the interfering metal ion and a thermodynamically-unstable complexing agent, then processing the solution by separating and removing harmful or valuable metal ions from the solution at a temperature below the decomposition temperature of the thermodynamically-unstable complexing agent, then subsequently heating a solution to a sufficiently elevated temperature and/or adding a mild oxidizing agent to decompose the metal complex and the thermodynamically-unstable complexing agent.

EXAMPLE

To Design a Separation Scheme for Metal Ions

The preventive complexing agents are particularly useful to "clean" the solvents used in the TRUEX process for disposal of radioactive wastes.

The following Table lists distribution coefficients for plutonium, uranium and americium between a TRUEX process solvent containing 0.2 molar octyl(phenyl)-N,N-diisobutylcarbamoylmethylphosphine oxide and 1.2 molar tributyl phosphate in dodecane and various concentrations of nitric acid at 25° C.

By adjusting the $HNO_3$ molarity one can easily, selectively remove a desired component by partitioning it between the organic and aqueous phases.

| $HNO_3$ Molarity | Distribution Coefficient (organic/aqueous) | | | | | |
|---|---|---|---|---|---|---|
| | Uranium | | Plutonium | | Americium | |
| | A | B | A | B | A | B |
| $1 \times 10^{-1}$ | $5.0 \times 10^1$ | $8.0 \times 10^{-4}$ | $4.0 \times 10^1$ | $1.2 \times 10^{-4}$ | 1.0 | $8 \times 10^{-5}$ |
| $5 \times 10^{-1}$ | $3.3 \times 10^2$ | $2.5 \times 10^{-2}$ | $2.6 \times 10^3$ | $1.1 \times 10^{-3}$ | $1.2 \times 10^1$ | $6.8 \times 10^{-1}$ |
| 1 | $5.4 \times 10^2$ | $1.4 \times 10^{-1}$ | $9.8 \times 10^3$ | $4.0 \times 10^{-3}$ | $2.0 \times 10^1$ | 3.5 |
| 5 | $2.8 \times 10^3$ | 7 | $5 \times 10^4$ | $4.0 \times 10^{-1}$ | $2.2 \times 10^1$ | 9.0 |

This data also demonstrates the efficiency of vinylidene-1,1-diphosphonic acid in stripping metal ions from the organic solvent. As noted above, by selection of appropriate conditions from data such as the data shown in the Table above, one can strip all of the metal ions together or carry out selective stripping to recover them separately.

EXAMPLE

Removal of metal ion contaminants from aqueous solutions

Aqueous solutions of the thermodynamically-unstable complexing agents of the present invention can be used in commercially available supported liquid membrane-based modules to strip metal ion contaminants from aqueous solution. Other devices using a porous membrane separating means can also be used. In general the aqueous solution containing uranium is in contact with one side of the porous membrane and the aqueous solution of the complexing agent is in contact with the other. A known organic extractant is permeated into the pores of the membrane to carry the metal ions from one side to the other. The aqueous solution of the complexing agent strips metal ions from the organic extractant in the pores, driving the extraction "reaction" toward removal of metal ions from the solution to be decontaminated.

Removal of Uranium from Groundwater

Aqueous solutions of the thermodynamically-unstable complexing agent described in this application are useful as stripping agents in a supported liquid membrane-based process for removal of uranium contaminants from groundwater. In this process, groundwater containing $10^{-4}M$ uranium is acidified to pH of 2 by addition of small amounts of sulfuric acid and passed through porous polypropylene hollow fibers in a supported liquid membrane module. The pores of the membrane are filled with 0.1M bis(2,4,4-trimethylpentyl)phosphinic acid in n-dodecane. The stripping solution, containing 0.25M VDPA, is circulated outside the hollow fibers and interacts with the organic extractant in the pores to remove metal ions therefrom.

Uranium levels in the groundwater were found to be reduced to $10^{-8}$M. The strip solution was found to contain $10^{-1}$M uranium. The VDPA was destroyed by heating to 60° to 70° C. overnight (about 5 hours) to produce a substantially organic-free uranium-containing product for recovery or disposal.

EXAMPLE

Removal of Metal Ions from a Solid Substrate and in Particular, Decontaminating Tools and Equipment Associated with Nuclear Reactors.

If an aqueous solution of the inventive complexing agent is contacted with metal ions on the surface of a solid substrate, the ions can be complexed and solubilized for removal. An acid solution can be used for this purpose.

The primary use of this method is expected to be for decontamination of equipment or tools associated with nuclear reactors. One difficulty, is to ensure contact with ions "embedded" in the surface to be decontaminated. This usually requires destruction or dissolution of a surface oxide layer when the surface is metal. The following uses an Fe(O)OH mineral to show that this is practical. This oxide of iron is considered one of the more difficult to penetrate.

To stimulate breaking of an oxide layer to allow decontamination, 100 mg samples of Goethite, an Fe(O)OH mineral, were contacted with 0.5M solutions of VDPA, malonic acid or maleic acid at 80° C. for four hours. The VDPA solution dissolved 40% of the Goethite. The malonic and maleic acids only dissolved 8% and 2% respectively.

Obviously, many modifications and variations of the invention as hereinbefore set forth can be made without departing from the spirit and scope thereof and therefore only such limitations should be imposed as are indicated by the appended claims.

What is claimed is:

1. A method of removing metal ions from a non-aqueous medium comprising
   (a) reacting the metal ions with a thermodynamically-unstable water soluble complexing agent in an aqueous solution to form a water-soluble metal complex, thereby removing metal ions from the non-aqueous medium into the aqueous solution; and thereafter
   (b) decomposing the complexing agent into inorganic compounds thereby to destroy the water-soluble complex and release the metal ions in a substantially organic free form; and wherein the thermodynamically-unstable complexing agent has the formula:

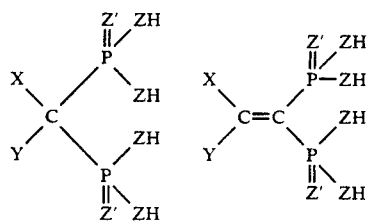

wherein the X and Y substituents are each selected from the group consisting of —H, halogen, —Z"H, —CO$_2$H, —CH$_2$Z"H, —CH$_3$, —CH$_2$CH$_3$, —CH$_2$NH$_2$, —CONH$_2$, —CH$_2$Cl, —CH$_2$Br, —CH$_2$F, —CH$_2$I, —CH$_2$NO$_2$, —CH$_{12}$CN, —CH$_2$OR, —CH$_2$SR,

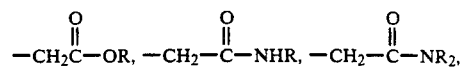

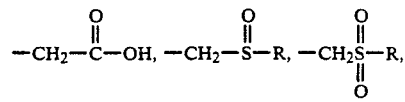

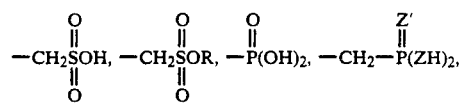

and —CH(PO$_3$H$_2$)$_2$, wherein

R is an alkyl group with one to three carbon atoms;

Z is oxygen or sulphur;

Z' is oxygen or sulphur; and

Z" is oxygen or sulphur;

or a water soluble salt thereof.

2. The method of claim 1 wherein the complexing agent is in the form of a sodium or potassium salt.

3. The method of claim 1 wherein at least one of Z, Z' and Z" is sulfur.

4. The method of claim 3 wherein the X substituent and the Y substituent are identical.

5. The method of claim 3 wherein the X substituent and the Y substituent are different.

6. The method of claim 3 wherein the complexing agent is

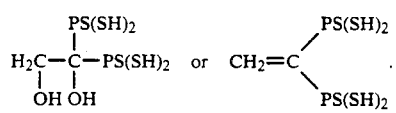

7. The method of claim 1 wherein Z, Z' and Z" are all oxygen.

8. The method of claim 7 wherein the X substituent and the Y substituent are identical.

9. The method of claim 7 wherein the X substituent and the Y substituent are different.

10. The method of claim 7 wherein the complexing agent is

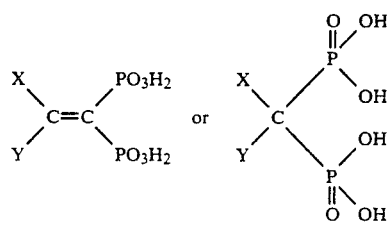

11. The method of claim 7 wherein the complexing agent is:

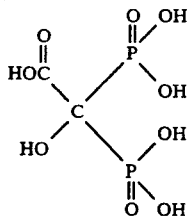

wherein the X and Y substituents are each selected from the group consisting of —H, halogen, —Z"H, —CO$_2$H, —CH$_2$Z"H, —CH$_3$, —CH$_2$CH$_3$, —CH$_2$NH$_2$, —CONH$_2$, —CH$_2$Cl, —CH$_2$Be, —CH$_2$F, —CH$_2$I, —CH$_2$NO$_2$, —CH$_2$CN, —CH$_2$OR, —CH$_2$SR,

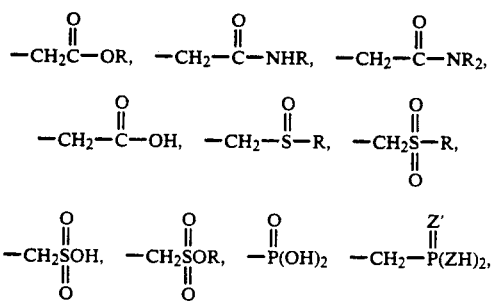

and —CH(PO$_3$H$_2$)$_2$, wherein
R is an alkyl group with one to three carbon atoms;
Z is oxygen or sulphur;
Z' is oxygen or sulphur; and
Z" is oxygen or sulphur;
or a salt, ester or thioester thereof and thereafter decomposing the complexing agent into inorganic compounds thereby to destroy the water-soluble complex and release the metal ions in a substantially organic free form.

12. The method of claim 1 further comprising removing the metal ion from the aqueous solution by precipitation as an insoluble salt.

13. The method of claim 12 wherein the insoluble salt is a phosphate salt.

14. The method of claim 1 wherein the complexing agent is decomposed by heating to from about 50° C. up to the boiling point of the aqueous medium, for at least about 5 minutes.

15. The method of claim 1 wherein decomposing of the metal ion complex comprises contacting the metal ion complex with an oxidizing agent under mild oxidizing conditions.

16. The method of claim 15 wherein the oxidizing agent is hydrogen peroxide, nitric acid, nitrous acid, hypochlorite ion, chlorine dioxide, peroxycarboxylic acids, or alkyl hydroperoxides.

17. The method of claim 1 wherein the non-aqueous medium comprises a hydrocarbon solvent containing an alkylamine, dialkyl amine, trialkyl amine or a neutral or acidic organophosphorus extractant.

18. The method of claim 1 wherein the non-aqueous medium comprises a hydrocarbon solvent containing bis(2-ethylhexyl) phosphoric acid, octyl(phenyl)-N,N-diisobutylcarbamoylmethylphosphine oxide, tributyl phosphate, or trioctyl amine, mono(2-ethylhexyl)2-ethylhexyl phosphonic acid, bis(2,5,5-trimethylpentyl)-phosphinic acid or a mixture thereof.

19. The method of claim 1 wherein the aqueous solution has a pH in the range of from about 2 to pH of about 7 molar in strong acid.

20. The method of claim 19 wherein the strong acid is sulphuric acid, perchloric acid, nitric acid or hydrochloric acid.

21. The method of claim 1 wherein the aqueous solution is a radioactive nuclear waste stream, a waste brine solution, or feed solution for hydrometallurgical processing.

22. The method of claim 1 wherein the metal ion is plutonium, neptunium, americium, or curium.

23. The method of claim 1 wherein the metal ion is strontium or cesium.

24. The method of claim 1 wherein the metal ion is iron, aluminum, cobalt, copper, or nickel.

25. The method of claim 7 wherein the non-aqueous medium comprises an alkylphosphonic acid, a dialkylphosphinic acid, an ester of phosphoric acid, and ester of an alkylphosphonic acid, an ester of a dialkylphosphinic acid or a trialkylphosphine oxide.

26. The method of claim 7 wherein the non-aqueous medium comprises tributyl phosphate, mono(2-ethylhexyl) 2-ethylhexylphosphonic acid or bis(2-ethylhexyl) phosphoric acid.

27. The method of claim 7 wherein the non-aqueous medium comprises octyl(phenyl)-N,N-diisobutylcarbamoylmethylphosphine oxide.

28. The method of claim 7 wherein the non-aqueous medium comprises an alkylamine solvent, a dialkylamine solvent, or a trialkylamine solvent.

29. The method of claim 28 wherein the alkylamine solvent is trioctylamine.

30. The method of claim 1 further comprising removing the metal ions released into the aqueous solution by liquid-liquid extraction.

31. The method of claim 1 further comprising removing the first metal ion from the aqueous solution by precipitation as an insoluble salt.

32. The method of claim 1 wherein the salt is a phosphate salt.

33. The method of claim 1 wherein the complexing agent is decomposed under mild oxidizing conditions or by heating to at least about 50° C. for at least about 5 minutes.

34. The method of claim 1, wherein the complexing agent is vinylidene diphosphonic acid, 1,2-dihydroxyethane-1,1-diphosphonic acid and 1-hydroxyethyl-1,1-diphosphonic acid.

* * * * *

UNITED STATES PATENT AND TRADEMARK OFFICE
CERTIFICATE OF CORRECTION

PATENT NO.   :   5,332,531
DATED        :   July 26, 1994
INVENTOR(S)  :   Earl P. Horwitz et al It is certified that error appears in the above-indentified patent and that said Letters Patent is hereby corrected as shown below:

Column 29, at the end of line 10: insert -- . --.

Column 30, line 28: change "and ester" to --an ester--.

Signed and Sealed this

Eighth Day of July, 1997

Attest:

BRUCE LEHMAN

*Attesting Officer*          *Commissioner of Patents and Trademarks*